US010849925B2

(12) United States Patent
Pittarello et al.

(10) Patent No.: US 10,849,925 B2
(45) Date of Patent: Dec. 1, 2020

(54) PROCESS FOR THE PREPARATION AND PURIFICATION OF THE SODIUM SALT OF HYALURONIC ACID

(71) Applicant: FIDIA FARMACEUTICI S.p.A., Abano Terme (PD) (IT)

(72) Inventors: Mara Pittarello, Abano Terme (IT); Francesco Borile, Abano Terme (IT); Vincenza Corsa, Abano Terme (IT)

(73) Assignee: FIDIA FARMACEUTICI S.P.A., Abano Terme (IT)

( * ) Notice: Subject to any disclaimer, the term of this patent is extended or adjusted under 35 U.S.C. 154(b) by 0 days.

(21) Appl. No.: 16/313,409

(22) PCT Filed: Jul. 27, 2017

(86) PCT No.: PCT/IB2017/054577
§ 371 (c)(1),
(2) Date: Dec. 26, 2018

(87) PCT Pub. No.: WO2018/020458
PCT Pub. Date: Feb. 1, 2018

(65) Prior Publication Data
US 2019/0224232 A1    Jul. 25, 2019

(30) Foreign Application Priority Data
Jul. 28, 2016  (IT) ........................ 102016000079633

(51) Int. Cl.
C08B 37/08    (2006.01)
C12P 19/04    (2006.01)
A61K 31/728   (2006.01)
A61P 41/00    (2006.01)
A61P 19/02    (2006.01)
A61P 27/00    (2006.01)

(52) U.S. Cl.
CPC ............ *A61K 31/728* (2013.01); *A61P 19/02* (2018.01); *A61P 27/00* (2018.01); *A61P 41/00* (2018.01); *C08B 37/0072* (2013.01); *C12P 19/04* (2013.01)

(58) Field of Classification Search
None
See application file for complete search history.

(56) References Cited

U.S. PATENT DOCUMENTS 7,575,914 B2 *  8/2009  Han ..................... C12P 19/26
                                                435/253.4
2002/0120132 A1  8/2002  Prescott

FOREIGN PATENT DOCUMENTS

EP        0716688 B1 *  9/2003  ......... C08B 37/0072
WO        WO 86/04355 A1   7/1986
WO        WO 92/18543 A1  10/1992

OTHER PUBLICATIONS

International Search Report issued in PCT/IB2017/054577 (PCT/ISA/210), dated Nov. 6, 2017.
Written Opinion of the International Searching Authority issued in PCT/IB2017/054577 (PCT/ISA/237), dated Nov. 6, 2017.

* cited by examiner

*Primary Examiner* — Layla D Berry
(74) *Attorney, Agent, or Firm* — Birch, Stewart, Kolasch & Birch, LLP

(57) ABSTRACT

The present invention concerns a process for the preparation and purification of the sodium salt of HA from the fermentation broth of *Streptococcus* or *Bacillus* or from rooster combs, the sodium salt of HA obtained and purified with said process and pharmaceutical, cosmetic and nutritional compositions comprising said sodium salt of HA.

25 Claims, No Drawings

PROCESS FOR THE PREPARATION AND PURIFICATION OF THE SODIUM SALT OF HYALURONIC ACID

The present invention concerns a process for the preparation and purification of the sodium salt of hyaluronic acid.

FIELD OF THE INVENTION

Hyaluronic acid (HA) is a high-molecular-weight linear, anionic polysaccharide, free of sulfate groups, consisting of alternating residues of D-glucuronic acid and N-acetyl-D-glucosamine.

It is present in nature in pericellular gels, in the fundamental substance of the connective tissue of vertebrate organisms (of which it represents one of the main components), in the synovial fluid of articulations, in the vitreous humor and in the umbilical cord.

HA therefore plays an important role in the biological organism, above all as a mechanical support of cells of numerous tissues, such as skin, tendons, muscles and cartilage.

It is also known that HA, through its membrane receptors, in particular CD44, CD54 and CD168, modulates many different processes relating to the physiology and biology of cells, such as, for example, proliferation, migration, cell differentiation and angiogenesis, and which also exerts other functions such as the hydration of tissues and lubrication of the articulations. It is absolutely biocompatible and, thanks to its numerous special features, is widely used in various fields, from tissue repair to viscous additional therapy, from dermo-aesthetic medicine to the intraocular surgery, from tissue engineering to cell therapy, and much more.

The physico-chemical and biological features of HA are strongly correlated to its molecular weight (MW) which is extremely variable: it can generally be asserted that the weight average MW of HA ranges from 20,000 to $13 \times 10^6$ Da approximately, and this approximation is necessary as it changes radically in relation to the source and production and purification method used for isolating it.

There are fundamentally two main methods for obtaining HA:

production from animal source: historically HA is extracted from animal tissues such as the umbilical cord, vitreous humour or bovine synovial liquid and, above all, rooster combs. Its production from animal source has many limitations, it is expensive, for example, as numerous passages are necessary for eliminating various types of impurities (starting from the mass of organic residues after the digestion of the starting tissue), it therefore requires passages which ensure the inactivation and elimination of any contaminant agent (such as viruses) possibly present in the starting material, it requires the availability of considerable quantities of raw material and does not produce great yields;

fermentation of microorganisms: some microorganisms, in particular of the genus *Streptococcus* or *Pasteurella*, suitably stimulated and/or modified, are capable of producing HA which is secreted in the culture broth from which it is isolated through various processes known to skilled persons in the field. Also in this case, numerous passages are necessary for eliminating the "impurities" present such as, for example, the residues of the cell walls of the microorganisms used, metal ions, nucleic acids and any other undesired proteinaceous material. In spite of these limitations, this is, to date, the most developed and widely used production method of HA. New methods are being studied for the production of HA via bio-technology, through the transfection of genes expressing the enzyme HA-synthases in suitable host cells, such as some kinds of *Bacillus* (*Megaterium* and *Sibtilis*) and in *Escherichia coli*. All procedures suitable for eliminating any potentially harmful residue are however also necessary for these production methods.

In any case, regardless of the method used, a key passage in the production of HA is obviously the extraction and purification phase of the polysaccharide. The known methods are numerous and extremely articulated, obviously modulated with respect to the starting sources for obtaining HA. First of all, the residues of the source must be eliminated, consequently, for extraction from animal tissue there are digestion phases of the proteins, and subsequent filtrations, centrifugations and washings; for the fermentation, centrifugations and progressive washings are normally used. In any case, a liquid fraction is obtained, from which the polysaccharide is isolated. In this respect, the best known and certainly most widely-applied procedure, above all for HA from animal sources, is precipitation with solvents: in short, increasing concentrations of organic solvents (ethanol, acetone) are used on the liquid fraction mentioned above, which cause the precipitation of the hyaluronic acid, which is then purified by means of subsequent solubilizations and precipitations.

An alternative system envisages the use of quaternary salts, cetylpyridinium or cetyltrimethylammonium with the aim of complexing the polysaccharide and causing its precipitation. Subsequent solubilizations and precipitations are again necessary before obtaining the final product.

The development of techniques has also combined the key steps described above, so as to make the process efficient in terms of yield and effective in terms of purity: to date, however, there are still numerous adverse events, in the order of a few hundreds, reported to the competent authorities (such as FDA) that have arisen especially after administration of injectable pharmaceutical compositions based on HA.

This polysaccharide is used in a wide variety of fields and pathologies: from cosmetic applications (by topical or oral administration) with a moisturizing action, to topical dermocosmetic use having a soothing effect, from injecting devices for the correction of skin defects (intradermal) whether they be wrinkles or scars, up to more strictly pharmacological applications such as intra-articular use in bone and joint diseases, or intraocular use as a substitute for the vitreous humour, and so forth.

Whereas for cosmetic applications, which do not involve damaged tissues, a cosmetic-grade HA (less pure) is sufficient, it is evident however, that in the case of injectable pharmaceutical applications (especially in closed cavities such as articulation and the eye), a degree of absolute purity is necessary: the presence of various types of contaminants, such as nucleic acids and/or proteins and/or residual bacterial toxins of the cell walls of Gram-positives such as lipoteichoic acid LTA (for example of the genus *Bacillus, Streptococcus, Enterococcus* and *Staphylococcus*) or of Gram-negatives such as lipopolysaccharide LPS (such as, for example, *Escherichia Coli, Pasteurella* and *Salmonella*), can cause a significant inflammatory reaction with the consequent release of cytokines (in particular TNF and IL-1) at both a local and systemic level, which could trigger a generalized inflammatory reaction with repercussions in the whole organism, reaching (in the most serious cases) forms of septic shock, and this explains the numerous reports of adverse events cited above. LTA and LPS, in fact, are polymers consisting of a lipid portion and a saccharide portion capable of causing strong immune responses and, in the most serious cases, arthritis, nephritis, meningitis or causing fever and shock with consequences that can even be fatal.

It should also be taken into account that, as previously mentioned, the MW of HA varies in relation to the source and production method. More specifically, the MW indicated to herein, refers to the weight average molecular weight measured with the "intrinsic viscosity" method. The variability of the MW determines the use of HA in different fields: for example, low MWs are applied in dermatological or dermocosmetic preparations (about 200 kDA; Connectivine®), whereas for intra-articular applications, higher molecular weights are preferred (normally within the range of 700-1800 kDA; Hyalgan®, Hyalubrix® Orthovisc®) up to MWs of over 1500 kDA used in plastic surgery or intraocular applications. It is extremely important to perfectly calibrate the MW of HA, not only because it determines the biological and physico-chemical characteristics of the polymer, but also because it has been amply demonstrated that HA having a MW lower than 30,000 Da has a strong inflammatory effect (EPO 138572), which is absolutely undesirable, regardless of the application.

This means that in the production and purification process of HA, various factors must be evaluated and controlled:
- the process yield: it is fundamental to extract the maximum possible amount of HA from the production source selected;
- the accuracy of the ensemble of the purification steps: the product obtained must be free of any contaminant capable of triggering inflammatory processes;
- the fractionation of the MW: the desired MW and certainty of having eliminated the inflammatory fractions must be obtained.

Numerous attempts at combining these requirements are known in the state of the art. Among these the following can be schematically mentioned:

U.S. Pat. No. 5,925,626: purification of HA from rooster combs by precipitation with ethanol and formation of two MW fractions (50-100 kDa and 500-730 kDa), free of the inflammatory fraction;

EP535200: purification of HA from rooster combs by salification with quaternary amines and subsequent solvent precipitation (ethanol or acetone). A HA is obtained having a MW ranging from 750 to 1230 kDa, free of inflammatory fractions and specifically destined for ophthalmic use;

U.S. Pat. No. 6,489,467: purification of HA from *Streptococcus* by forced acidification using HCl, with subsequent variations in the pH and diafiltrations obtaining HA having a MW of about 1700 kDa;

Choi et al. *Biomaterials Research*, 2014, 18, 1-10: purification of HA from *Streptococcus zooepidemicus* by diafiltration and precipitation with acetone. A HA with a MW ranging from 900 to 1100 kDa is obtained;

EP2870255: purification of HA from *Streptococcus zooepidemicus* by filtrations and ultrafiltrations, pH variations reaching a MW ranging from 60 to 2400 kDa, and final precipitation with ethanol.

DETAILED DESCRIPTION OF THE INVENTION

An object of the present invention relates to a new process for the preparation and purification of a sodium salt of HA which allows its production with
- a very high purity degree as it is free of contaminants and
- a precise and specific MW.

The new purification process of hyaluronic acid and its sodium salt comprises various steps, articulated and sequential, for the purification of a HA prepared as widely known to skilled persons in the field: from both a biological source, in particular from bird crests of the genus *Gallus* (EP0138572, hereinafter these crests will be indicated as rooster combs, regardless of the gender of the bird) and also from the fermentation process of Streptococco, also applicable to a HA prepared with molecular engineering techniques from *Bacillus Subtilis* and *Bacillus Megaterium* (EP 2614088, EP2614087); this process is preferably applicable to a HA obtained from the fermentation broth of *Streptococcus*, even more preferably from the broth of *Streptococcus equi* sub-sp. *equi,* 68222, mutant H-1 (EP0716688). The Applicant has demonstrated hereunder how this process allows the preparation not only of a sodium salt of HA in conformance with all the physico-chemical specifications required by the European Pharmacopoeia (monography of HA: *Ph, Eur,* 5.0, January 2005: 1472) but, in particular, for some purity characteristics, the specifications claimed by the Applicant have been further restricted, in order to guarantee a hyaluronic acid having a very high degree of purity, which can be used in complete safety especially in all injectable pharmaceutical compositions (intra-articular, intradermal and intraocular) as it is free of any pro-inflammatory and pyrogenic component. The sodium salt of HA purified by means of the new process object of the invention, can also be used in the preparation of all the derivatives known to skilled persons in the field, such as, for example, its salts with heavy metals (EP 0827514), esters (EP 0216453), amides (EP 1095064) sulfonates (EP0940410) and cross-linked products, among which self-crosslinked products (EP0341745).

An object of the invention also relates to particular thermal treatment phases of HA still to be purified, in particular the fermentation broth of *Streptococcus* (containing this HA), in order to obtain different fractions of HA having a precise weight average MW: the Applicant has in fact perfected specific thermal treatment in terms of temperature and treatment time (conditions described in detail hereunder) which follow the inactivation phase of the fermentation broth or which take place contemporaneously with the enzymatic digestion of the rooster combs, which allow a final product having the desired intrinsic viscosity, to be obtained. Specific weight average MW values of HA correspond to specific values of the intrinsic viscosity, and this viscosity is calculated according to what is written in the corresponding monography of HA of the European Pharmacopoeia according to the "intrinsic viscosity" method (*Ph. Eur.* 5.0, January 2005: 1472).

A further object of the invention relates to pharmaceutical, cosmetic and nutritional compositions containing said fractions, more specifically:
- pharmaceutical compositions for intra-articular use containing sodium salt of HA with a very high/high/medium weight average MW to be used in the visco-supplementation of arthritic joints, in traumatic joint damage, in subchondral damage;
- pharmaceutical compositions for intraocular use or for ocular administration for the treatment of eye diseases, containing sodium salt of HA with a very high/high/medium/low weight average MW;
- pharmaceutical compositions containing sodium salt of HA with a very high/high/medium/low weight average MW to be used in the prevention of post-surgical adhesions;

pharmaceutical compositions for topical or injective use (intradermal and/or intramuscular) containing sodium salt of HA with a very high/high/medium/low weight average MW, preferably sodium salt of HA with a medium/low weight average MW, in the treatment of skin ulcers, bedsores, burns, scars and skin lesions, in the treatment of keloids or hypo/hypertrophic scars, therefore in the treatment of all types of skin defects with intact or damaged skin, and as a therapy for the treatment of skin diseases such as eczemas and various kinds of dermatitis, in particular atopic dermatitis and nappy rash, psoriasis;

pharmaceutical compositions for intravesical use containing sodium salt of HA with a very high/high/medium weight average MW, in particular for the treatment of interstitial cystitis;

pharmaceutical compositions for injective use containing sodium salt of HA with a very high/high/medium weight average MW as a filler in the dermo-aesthetic field or as body shaping in plastic surgery;

cosmetic compositions for topical and oral use;

pharmaceutical or nutritional compositions containing sodium salt of HA with a very high/high/medium/low weight average MW for the oral treatment or arthritic joints, for tendon trophism, skin trophism and of the gastrointestinal mucous membrane.

A further object of the invention also relates to two/three-dimensional biomaterials comprising derivatives prepared with HA purified according to the invention, in the form of pads, woven, non-woven fabrics, granulates, films and gels, also in possible association with cells of various origins and/or blood components, such as, for example, platelet-derivatives. The Applicant has perfected the following purification process with the main objective of eliminating all the impurities deriving from the selected production source of hyaluronic acid, mainly represented by proteins, nucleic acids and/or by other/various kinds of pyrogens. In particular, the objective of the present invention is the complete elimination of bacterial toxins deriving from Gram-positive bacteria such as *Streptococcus* or *Bacillus* (or from bacteria such as, for example, Enterococci and Staphylococci) or from Gram-negative bacteria such as, for example *Escherichia Coli* (or *Pasteurella* and *Salmonella*) normally absent in the fermentation broths (if not residual from the source strain) but whose possible contamination would represent a very important safety problem: the presence of toxins (such as LTA or LPS) in HA as end-product would in fact deprive it of the necessary purity required, as it can determine the production of highly pro-inflammatory factors that could cause inflammation/infection of the joints or tissues treated, even up to their total destruction or necrosis.

The new purification process of the sodium salt of HA ensures:
a high process yield
total purity of the product
production of the fraction with the desired intrinsic viscosity (therefore MW).

The process consists of two or three steps:
inactivation (this step is present only for the production of HA from the fermentation broth of *Bacillus* and of *Strepococcus*);
extraction;
purification.

Inactivation: this step relates to the production of HA from *Streptococcus* (and also from *Bacillus*) which is fermented in specific fermenters containing suitable culture mediums under the conditions known to skilled persons in the field; this process is followed by the inactivation phase of the bacteria by acidification of the culture broth, preferably with HCl, in order to decrease the pH to a value between 4 and 5, at this value in fact *Streptococcus* completely ceases its metabolic activity.

This is followed by the thermal treatment of the inactive broth by heating (described hereunder) for the production of a HA having a high or medium viscosity or with a low viscosity; this treatment is not effected in the case of the production of HA having a very high viscosity. As indicated above, in fact, specific MW ranges correspond to specific viscosity ranges and in this way the Applicant has developed a process which allows the production of the desired fractions with absolute precision, as demonstrated hereunder.

The biomass is eliminated by filtering the inactivated broth on pads of Celite (diatomaceous earth, chemical name: silica dioxide), with a possible further subsequent filtration through a filter with a filtration degree equal to 0.5 μm (propylene filters are preferable); the broth is preferably neutralized with soda (NaOH) at a pH of 6.5-7.5.

Extraction: this phase is in common for both the production of HA from *Streptococcus* and *Bacillus* and for HA obtained from rooster combs; in the latter case, the process according to the invention starts from the homogenate obtained from combs according to what is described in EP 0138572. More specifically, the homogenate, is subjected to thermal treatment by heating (described hereunder) for the production of a HA having a high or medium or low viscosity; this thermal treatment is effected contemporaneously with the enzymatic digestion (to which said homogenate—hereinafter defined as enzymatic digested homogenate—is subjected) with the enzyme papain prepared in a phosphate buffer, as known to skilled persons in the field. The non-purified hyaluronic acid present in the neutralized filtrate or present in the mixture of enzymatic digest subjected to thermal treatment (hereinafter defined as medium containing non-purified HA), is subsequently complexed with CPC (Cetyl Pyridinium Chloride, the CPC-HA salt is formed) after a further addition of Celite under stirring. The complex is left to settle to separate the solid from the liquid phase which is eliminated. The HA present in the solid phase is then solubilized under stirring, with a NaCl saline solution and the product obtained (sodium salt of HA soluble in this medium), is subjected to further filtrations/purifications by means of filtering cloths to separate the residual Celite and by means of filters with a filtration degree equal to 3 μm (polypropylene filters are preferred), collecting the filtrate. This particular procedure is defined as "extraction" of the sodium salt of HA not yet purified, and can be effected from 1 to 4 times. After collecting and joining the filtered products, the so "extracted" product is treated with particular resins of the aromatic type suitable for absorbing large-sized molecules thanks to the pore radius ranging from 200 to 300 Angstrom, they decisively contribute to lowering the total impurity of HA deriving from the system of origin from which the polysaccharide was purified and also from the substances used in the above process. The resin consisting of crosslinked polystyrene matrixes is preferably used, the resin DIAION HP20 (or HP20L) (MITSUBISHI CHEMICAL) has proved to be particularly efficient. Said treatment consists of leaving resin and extract under stirring for a period of time. The product obtained is then filtered by means of filters/cloths preferably made of polypropylene (to separate the resins from the HA sodium salt), possibly also on 3 μm-filtration degree filters.

Purification: this final step can be possibly preceded by the precipitation in ethanol of the sodium salt of HA obtained in the extraction" phase (this step can be introduced in order to further purify the polysaccharide, especially when it comes from rooster combs); the elimination of the above solvent is followed by the re-solubilization of the precipitate in water, subsequently proceeding with the following "purification" steps: addition of NaOH in water for the total elimination of the residual toxins, neutralization, preferably with HCl (at 37% by weight), up to a pH ranging from 8 to 9 (the term "neutralization" is simply used in this phase for indicating the Applicant's intention of lowering the pH to values closer to neutrality), filtration preferably by means of filters having a filtration degree of 3 µm, precipitation and at least a washing with ethanol, final washing in an organic solvent, preferably acetone. The sodium salt of HA thus produced and purified is dried as known to skilled persons in the field.

An object of the present invention therefore relates to the preparation and purification process of the sodium salt of HA schematized hereunder in its phases:

A. Inactivation (for the purification of a HA produced from the fermentation of *Streptococcus* and *Bacillus*):
  A1. acidification of the fermentation broth to a pH of 4-5; HCl 1N is preferably used;
  A2. thermal treatment of the broth, under stirring (this treatment is not effected if a HA with a very high viscosity is produced);
  A3. elimination of the biomass by means of filtration on pads of Celite (chemical name: silica dioxide; in an amount of from 20 to 60 g/litre of broth, preferably 30-40 g/litre), possible further filtration with filters having a filtration degree of 0.5 µm, preferably polypropylene filters;
  A4. neutralization to pH 6.5-7.5, preferably with aqueous NaOH at 20%.

B. Extraction:
  in the case of homogenate from combs, the corresponding thermal treatment is first effected contemporaneously with its enzymatic digestion and subsequent filtration (to eliminate the undigested biological residue), followed by the following common phases:
  B1. addition of Celite (in an amount of from 20 to 60 g/litre of broth/litre of enzymatic digest, i.e. per litre of medium containing non-purified HA) and complexing with Cetyl Pyridinium Chloride (CPC) (4-20 g/litre/litre of enzymatic digest, preferably 5-15 g/litre), under stirring, for at least 30 minutes and subsequent sedimentation for at least 30 minutes;
  B2. elimination of the liquid phase;
  B3. solubilization of the HA present in the solid phase in NaCl (an 0.3M aqueous solution is preferably used) under stirring for a period of 4 to 24 h, filtration by means of filtering cloths to separate the residual Celite and filters with a filtration degree of 3 µm (polypropylene filters are preferred) and collection of the first extract as sodium salt of HA; this procedure should be repeated from 1 to 4 times;
  B4. joining the extracts;
  B5. addition to the joined extracts of a resin of the aromatic type (in an amount of from 10 to 60 g/litre of extract) with a pore radius of 200-300 Angstrom, the resin composed of crosslinked polystyrene matrixes is preferred, the resin DIAION HP20 (or HP20L) is even more preferred, this treatment is effected under stirring for at least 8 h;
  B6. at least a filtration by means of filtering cloths (preferably made of polypropylene) to separate the resins from the sodium salt of HA, and possibly at least a filtration with 3 µm-filtration degree filters (for this filtration, polypropylene filters are preferred).

C. Purification:
  in the case of the sodium salt of HA obtained from rooster combs, this step can be possibly preceded by the precipitation in ethanol of the sodium salt of HA obtained in the previous step, with the elimination of the above solvent and ri-solubilization of the precipitate in purified water (*Ph. Eur.* 8.0, January 2009:0008) to restore the starting volume and subsequently proceeding with the following purification phases, regardless of the source selected:
  C1. addition of NaOH (a 0.2-0.4 M solution is preferably used) in water, under stirring;
  C2. neutralization to a pH ranging from 8 to 9, preferably with HCl (at 37%);
  C3. filtration, a filter with a filtration degree of 3 µm is preferable (polypropylene filters are preferred);
  C4. precipitation and at least a washing of the sodium salt of HA sodium salt coming from step C3 with ethanol, final washing in an organic solvent, preferably acetone;
  C5. drying of the sodium salt of HA as known to skilled persons in the field, preferably from 25 to 40° C. for not less than 15 h, under vacuum.

Determination of the Weight Average MW of the Sodium Salt of HA

The thermal treatment object of the present invention allows the production of the sodium salt of HA with an intrinsic viscosity (IV) which falls within specific ranges (IV measured according to the method described in *Ph. Eur.* 5.0. January 2005; Ph. Eur. 1472), described hereunder:

Thermal Treatment of HA from Fermentation Broth of *Streptococcus* or *Bacillus*:
  60±5° C. for 5-40 minutes: this allows the production of a HA with a high viscosity, therefore a sodium salt of HA having a final IV within the range of 17-24 dl/g; the above thermal treatment is preferably carried out at 65° C. for 5-30 minutes;
  70±5° C. for 5-40 minutes: this allows the production of a HA with a medium viscosity, therefore a sodium salt of HA having a final IV within the range of 10-15 dl/g; the above thermal treatment is preferably carried out at 70° C. for 5-30 minutes;
  90±5° C. for 150-300 minutes: this allows the production of a HA with a low viscosity, therefore a sodium salt of HA having a final IV within the range of 3-6 dl/g;
  If the thermal treatment is not effected, the final IV of the sodium salt of HA, purified according to the object of invention, is equal to or over 29 dl/g, therefore the purified product is a sodium salt of HA having a very high viscosity.

Thermal Treatment of HA from Rooster Combs:
  50-60° C. for 26-30 h: this allows the production of a HA with a high viscosity, therefore a sodium salt of HA having a final IV within the range of 17-24 dl/g; the above thermal treatment is preferably carried out at 55° C. for 28 h;
  60-65° C. for 28-30 h: this allows the production of a HA with a medium viscosity, therefore a sodium salt of HA having a final IV within the range of 10-15 dl/g; the above thermal treatment is preferably carried out at 60° C. for 30 h;
  65-70° C. for 46-50 h: this allows the production of a HA with a low viscosity, therefore a sodium salt of HA having a final IV within the range of 3-6 dl/g; the above thermal treatment is preferably carried out at 65° C. for 48 h.

At the end of the treatment, a skilled person in the field can collect a sample and verify the viscosity obtained, on the basis of the result reached, he can either repeat the operation or modify the time and/or temperature of the treatment (still within the range described) in order to reach the desired viscosity: the treatment times and temperatures for reaching the ranges of IV described above depend, in fact, on the concentration and MW of the HA present in the initial broth/digest.

The Mark-Houwink equation (Terbojevich M. et al, *Carbohydrate Research*, 1986, 149, 363-377; Terbojevich M. et al, *Carbohydrate Research*, 1986, 157, 269-272) is used for specifying the corresponding average MWs, the equation relates the VI with the MW. Consequently, the viscosity ranges correspond to specific MW ranges:

29 dl/g corresponds to about 1885 kDa 17-24 dl/g corresponds to a range from about 920 to 1450 kDa 10-15 dl/g corresponds to a range from about 450 to 780 kDa 3-6 dl/g corresponds to a range from about 90 to 231 kDa.

With the following experimentation, the Applicant has demonstrated the efficacy of the process object of the invention, in terms of purity of the obtained sodium salt of HA Purification of the Sodium Salt of HA Produced from *Streptococcus*

At the end of the fermentation process of *Streptococcus equi* 68222 mutant H-1, fermented as in Example 3 of EP 0716688, about 5 litres of broth are collected and contaminated with *E. coli* ATCC 8739 in a quantity of $10^9$ bacterial cells per ml of broth. This broth is then left in an open container (in order to favour further contamination from bacteria or from yeast/fungi whose spores may be present in the air) for a time not shorter than 16 h, at room temperature. It is then divided into two samples: 2.5 litres (sample A) are subjected to the complete purification process object of the invention, whereas the remaining 2-5 litres (sample B) are subjected to simple precipitation, as described hereunder. A sample of broth is subjected to microbiological control by qualitative and quantitative analyses (by means of the API System effected according to *Ph. Eur.* 5.0; 2.6.12) of the microbial and/or mycotic charge present. The results are indicated in table A.

Sample A: the broth is subjected to inactivation by acidification to pH 4.3 with HCl 1 N and thermal treatment at 65° C. for 10 minutes, under stirring. The biomass is eliminated by filtration on Celite (40 g/l) and neutralized to pH 6.5 with aqueous NaOH at 20%. This is followed by the extraction phase with the addition of Celite (20 g/l of broth) and complexing with CPC (10 g/l of broth) under stirring for 30 minutes with subsequent sedimentation for 1 h; the liquid phase is then eliminated by siphoning and the HA present in the solid phase is solubilized in aqueous NaCl 0.3 M, still under stirring for a period of 20 hours; this process continues with filtration on a filtering cloth and also using filters with a filtration degree of 3 μm and the collection of the first extract; this procedure is repeated 2 times and the two extracts are joined; this is followed by the addition of a resin of the aromatic type, DIAION HP20 (40 g/l, this treatment is effected, under stirring, for 8 h) and filtration to separate the resins from the HA using polypropylene filtering cloths. The purification is carried out by adding NaOH 0.4 M in water (under stirring) and is followed by neutralization at pH 8.5 with HCl (37%) and by filtration with filters in polypropylene with a filtering degree of 3 μm. The sodium salt of HA is precipitated with ethanol 100%, washed with ethanol 80%, and the final washing is effected in acetone; the final drying of the sodium salt of HA obtained and purified, is effected at 25° C. for 20 h under vacuum.

Sample B: this sample was subjected to inactivation by acidification at pH 4.3 with HCl 1 N and thermal treatment at 65° C. for 10 minutes under stirring, exactly as for Sample A. The biomass was eliminated from the broth by filtration on Celite, the filtrate was then subjected to precipitation with ethanol with drying, at 25° C., of the HA (not purified) precipitated, for 20 h under vacuum.

The purified HA must be non-pyrogenic, i.e. there should be no elements that can cause an increase in the body temperature after its administration. The test for evaluating the non-pyrogenicity can be carried out in various ways: the LAL Test (for the specific determination in vitro of the endotoxin LPS deriving from Gram-negatives, required by *Ph. Eur.* 5.0 in the monography relating to Sodium Hyaluronate), the Pyrogen Test (non-discriminating analysis in vitro on the nature of the pyrogen agent) and Endosafe®-IPT (test in vitro not required by Pharmacopoeia).

LAL Test: the basis of the LAL test is the capacity of the amebocytes extracted from blood of *Limulus polyphemus* to gel in the presence of bacterial endotoxins from Gram-negatives, primarily responsible for the pyrogen effect. This test is carried out according to *Ph. Eur.* 5.0, 2.6.14.

Pyrogen Test: this test represents the most widely-used analysis method for determining the presence of pyrogen substances, it contemplates the use of rabbits into which a small dose of the product is injected in the outer ear vein, the baseline temperature is taken three hours after the injection. The rise in temperature is a sign of pyrogenicity of the product. This test is carried out according to *Ph. Eur.* 5.0, 2.6.8.

Endosafe®-IPT (Charles River Laboratories, Inc.): test capable of detecting the presence of pyrogens of any type as they can stimulate the production of cytokine IL-1β which is highly pro-inflammatory. This test allows the identification of pyrogens of both an endotoxic (LPS) or non-endotoxic nature (LTA and/or proteins and/or pyrogen derivatives, for example from viruses or yeast/mold): it consists of two steps, in the first step, the sample is incubated with human blood (if present, pyrogens stimulate the production of IL-1β by the monocytes of the blood), the second step consists of the detection of the presence of IL-1β produced by a specific test ELISA read at 450 nm (Schindler S. et al, *ALTEX*, 2009, 26, 265-277).

For samples A and B the analysis of the pyrogens was carried out using the Pyrogen Test and Endosafe®-IPT, as the LAL Test is not capable of evaluating the possible presence of pyrogen agents other than endotoxin LPS, whereas the other two methods reveal pyrogens of any nature, even if with different sensitivities. The IPT test, in fact, allows bacterial residues coming from both Gram-positives and Gram-negatives to be identified, and surpasses the Pyrogen Test as far as the sensitivity is concerned. Furthermore, the IPT is more specific than the test on rabbits as it evaluates the toxicity of the contaminants in human tissue (Hartung T. et al, *ATLA*, 2001, 29, 99-123). For both samples, the total protein content determined as from *Ph. Eur.* 5.0, January 2005; 1472, was also evaluated. The results of the tests are shown in table B.

Results

TABLE A in this table, the presence can be observed of an important bacterial and also mycotic charge in terms of non-pathogen organisms and pathogen organisms such as B. Cereus, Coli and Candida.

| | | |
|---|---|---|
| Microbial charge | Bacillus Cereus | $4.6 \times 10^7$/ml |
| | Streptococcus | $2.2 \times 10^7$/ml |
| | E. Coli | $9.8 \times 10^6$/ml |
| | Total charge | $7.8 \times 10^7$/ml |
| Mycotic charge | Mold | $9.4 \times 10^7$/ml |
| | Yeast (Candida Lusitaniae) | $2.5 \times 10^7$/ml |
| | Total charge | $1.2 \times 10^8$/ml |

The table therefore demonstrates how the initial broth specifically polluted contained pyrogen elements from both Gram-positives and Gram-negatives, in addition to various kinds of pyrogens, such as derivatives of Candida

TABLE B

| | Pyrogen Test | IPT | Protein content |
|---|---|---|---|
| Sample A | 0.9° C. | N.R. | 0.04% |
| Sample B | 4.1° C. | >5 EU/mg | 10% |

NR: non-detectable (lower than 0.05 EEU/mg)

These data show that the new purification process is capable of purifying HA from various kinds of pyrogen agents:

It can be noted from Table B that the IPT test of sample B shows a very high value of pyrogen toxins, the monography of HA Ph. Eur. 5.0, January 2005: 1472, in fact, allows, for injective administrations of HA, a maximum limit of endotoxins lower than 0.05 IU/mg (i.e. 0.05 EU/mg). In sample B, there is therefore a pyrogen concentration at least 100 times higher than this limit. In the three rabbits treated for the Pyrogen test, this concentration causes an overall temperature increase of 4.1° C. According to Ph. Eur. 5.0, 2.6.8, the product satisfies the Pyrogen test, if the sum of the three temperature rises does not exceed the value of 1.15°, therefore sample B proved to be strongly pyrogenic, thus confirming the data of the IPT test. Finally, this sample has a very high total protein % deriving from the mediums used for the fermentation of Streptococcus, and from the same bacteria not completely eliminated: monography of HA Ph. Eur. 5.0, January 2005: 1472 limits, by parenteral administrations, the overall proteins to a maximum value not exceeding 0.1%, therefore, also in this case, sample B has a protein value about 100 times higher than the limit value.

Sample A, purified according to the object of the invention, satisfies all the requirements for the injective administration of the sodium salt of HA: pyrogens in vivo with a temperature rise lower than 1.15° C., toxins in vitro lower than 0.05 EU/mg, and overall protein content lower than 0.1% (Ph. Eur. 5.0, January 2005: 1472).

This result demonstrates the effectiveness of the process object of the invention, as it ensures the total purification of the sodium salt of HA even from a particularly polluted sample, from both endotoxins and various kinds of pyrogens, guaranteeing the safety of the product which, in this way, satisfies all the requirements also in terms of more limiting purities, as demonstrated hereunder.

Example 1: Preparation and Purification of the Sodium Salt of HA from Streptococcus with IV within the Range of 10-15 dl/g At the end of the fermentation process of Streptococcus equi (68222 mutant H-1) fermented as per Example 3 of EP0716688), 5 litres of broth are inactivated by acidification to pH 4.5 with HCl 1N. This is followed by the thermal treatment of the broth with a temperature increase to 70° C. for 20 minutes under stirring. The broth is then filtered and poured into a Buchner filter in which 200 g of Celite were prepared on a filtering cloth. At the end of the filtration, the product is neutralized with aqueous NaOH 20% and the pH is fixed at 7.0. 100 g of diatomaceous earth and subsequently CPC in an amount equal to 11 g/l of broth, are added, under stirring, for 30 minutes, to the filtered broth. The whole mixture is left to rest for 40 minutes to allow the sedimentation of the newly formed CPC-HA complex. The liquid phase is eliminated by siphoning. The HA present in the solid phase is solubilized by means of a solution of aqueous NaCl 0.3M, under stirring for 10 h. The sodium salt of HA is finally filtered through a filtering cloth and filtering cartridges having a filtration degree of 3 μm (Pall). 200 g of Diaion HP20 resins are added to the extract which is left under stirring for 10 h. The whole mixture is filtered on propylene cloth and then, in sequence, through filters (Pall) with a 3 μm filtration degree. Aqueous NaOH is added to the solution of extracts, which is neutralized with HCl (at 37%), bringing the pH to a value of 8.5. The extracts are then filtered through a 3 μm-filtration degree filter. The solution of sodium salt of HA is precipitated with ethanol and kept under stirring for 30 minutes. The product is left to settle for 10 minutes and the supernatant is eliminated by siphoning. The product is washed with ethanol (under stirring for 10 minutes), and the supernatant is then eliminated by siphoning (in alternative, in case of broth quantities higher than 5 liters, the solid product is recovered by filtration on a filtering cloth). The last washing with acetone is carried out and the solid is recovered by filtration on a filtering cloth. The product obtained is positioned on suitable stainless steel trays and dried for 22 h at a temperature of 25° C. under vacuum.

Analysis of the product obtained (according to Ph. Eur. 5.0, January 2005: 1472):
IV: 14.5 dl/g (weight average MW: 748,000 Daltons)
Proteins: 0.02%
Bacterial endotoxins (LAL test): 0.012 EU/mg
Yield: for the determination of the total yield of the process object of the invention, the concentration is determined of HA in carbazole (Ph. Eur. 5.0, January 2005: 1472) present in the broth at the end of the fermentation, and is related to the final concentration of HA obtained at the end of the purification process (i.e. the ratio is calculated between the quantity in grams of end-product vs litres of broth at the end of the fermentation (then subjected to purification), a simple proportion is subsequently calculated to obtain the yield value expressed as percentage of purified HA vs initial HA to be purified).

In this case, 3.3 g/litre of HA were determined in the broth at the end of the fermentation, and 3.0 g/l of HA as purified product. The final yield was therefore higher than 90%.

Example 2: Preparation and Purification of the Sodium Salt of HA from Rooster Combs with IV within the Range of 10-15 dl/g 250 g of dry powder prepared from rooster combs as described in Example 1 of EP0138572, are mixed with 0.29 g of papain in 10 litres of dibasic sodium phosphate/dihydrate sodium phosphate/EDTA buffer (pH 6.5), under stirring for 10 minutes. This mixture is then subjected to thermal treatment by increasing its temperature to 60° C. for 30 hours. The resulting homogenate is then filtered and discharged into a Buchner in which 200 g of Celite have been prepared in a polypropylene filtering cloth. 200 g of Celite are added to the filtered product under stirring and then 2 litres of aqueous CPC solution (at 29 g/l) are added to said filtered product, leaving under stirring for 30 minutes. The mixture is then left to rest for 40 minutes to allow the sedimentation of the newly formed CPC-HA complex and the liquid phase is eliminated by siphoning. The HA present in the solid phase is solubilized with a solution of 4 litres of aqueous NaCl 0.3 M, under stirring for 10 hours. Finally, the sodium salt of HA is filtered through a filtering cloth and filtering cartridges having a filtration degree of 3 μm (Pall). At this point, 200 g of Diaion HP20L resins are added to the extract and the mixture is left under stirring for 10 hours. The whole mixture then is filtered on polypropylene cloth and subsequently, in sequence, through 3 μm-filtration degree filters (Pall). The sodium salt of HA is precipitated with 1.8 volumes of ethanol, under stirring for 30 minutes; the product is left to settle and the supernatant is eliminated by siphoning. The sedimented product is re-solubilized with 5 litres of purified water, under stirring.

Aqueous NaOH 0.2 M is added to the solution obtained, which is neutralized with HCl (37%), bringing the pH to 8.2. The filtration is continued using 3 μm-filtration degree filters. The sodium salt of HA obtained is then precipitated with ethanol under stirring for 30 minutes, the product is left to settle for 10 minutes and the supernatant is eliminated by siphoning. The product is washed with ethanol, the product is left to settle for 10 minutes and the supernatant is the eliminated by siphoning (in alternative, in case of broth quantities higher than 5 liters, the solid product is recovered by filtration on a filtering cloth). The last washing with acetone is carried out and the solid is recovered by filtration on a filtering cloth. The product obtained is positioned on suitable stainless steel trays and dried for 22 hours at a temperature of 40° C. under vacuum.

Analysis of the product obtained (according to Ph. Eur. 5.0, January 2005: 1472):
IV: 14 dl/g (weight average MW: 714,000 Daltons)
Proteins: 0.04%
Bacterial endotoxins (LAL test): 0.012 EU/mg
Yield: in this case, for the determination of the total process yield, the concentration of HA in carbazole is determined per litre of enzymatic digest, and is related to the final concentration of HA obtained at the end of the purification process (i.e. the ratio is calculated between the quantity in grams of the end-product vs litres of enzymatic digest (then subjected to purification), a simple proportion is then calculated to obtain the yield value expressed as percentage of purified HA vs initial HA to be purified).

In this case, the final yield of HA was higher than 85%.

Example 3: Preparation and Purification of the Sodium Salt of HA from *Streptococcus* with IV within the Range of 3-6 dl/g The procedure is the same as that described in Example 1, but the thermal treatment carried out is at 90° C. for 250 minutes. The final product is dried for 25 hours at 40° C., under vacuum.

Analysis of the product obtained (according to Ph. Eur. 5.0, January 2005: 1472):
IV: 5 dl/g (weight average MW: 181,000 Daltons)
Proteins: 0.015%
Bacterial endotoxins (LAL test): 0.0075 EU/mg
Yield: In this case, 3.3 g/litre of HA were determined in the broth at the end of the fermentation, and 2.5 g/litre as purified product. The final yield was therefore higher than 75%.

For this reason, a further object of the present invention relates to the purification process of HA wherein the maximum values of total proteins and toxins claimed for the sodium salt of HA, in addition to the total yield at the end of the process are:
–0.05% of proteins vs 0.1% established in Ph. Eur. 5.0, January 2005: 1472;
–002 IU/mg of endotoxins vs the maximum limit of 0.05 IU/mg allowed in Ph. Eur. 5.0, January 2005: 1472;
Yield: from 75 to 90%.

The invention claimed is:

1. A process for the preparation and purification of the sodium salt of HA from the fermentation broth of *Streptococcus* or *Bacillus* or from rooster combs comprising the following steps:
B. extraction, comprising the following steps:
B1. addition of Celite to a medium containing non-purified HA and complexing of HA with Cetyl Pyridinium Chloride (CPC), under stirring for at least 30 minutes and following sedimentation for at least further 30 minutes;
B2. elimination of the liquid phase formed in step B1;
B3. solubilization of the HA present in the solid phase in an aqueous solution of NaCl and collection of a first extract as sodium salt of HA; this procedure B3. being effected from 1 to 4 times;
B4. joining the extracts coming from step/s B3.;
B5. addition of an aromatic resin having a pore radius ranging from 200 to 300 Angstrom to the joined extracts of B4, the resin composed of crosslinked polystyrene matrixes being preferred, leaving under stirring for at least 8 hours;
B6. filtration of the mixture coming from step B5;
C. purification, comprising the following steps
C1. addition of an aqueous solution of NaOH to the filtrate obtained from step B6.;
C2. neutralization to a pH ranging from 8 to 9;
C3. at least one filtration;
C4. precipitation and at least one washing of the sodium salt of HA obtained in step C3. with ethanol, final washing in an organic solvent;
C5. drying of the sodium salt of HA, for not less than 15 h, under vacuum.

2. The process for the preparation and purification of the sodium salt of HA according to claim 1 wherein the fermentation broth of *Streptococcus* is a fermentation broth of *Streptococcus equi* sub specie equi 68222, mutant H-1.

3. The process for the preparation and purification of the sodium salt of HA from the fermentation broth of *Streptococcus* or *Bacillus* according to claim 1, wherein the process comprises a previous initial step of inactivation A. of the fermentation broth, comprising the following steps:
A1. acidification of the fermentation broth to pH 4-5;
A2. elimination of the biomass from *Streptococcus* or *Bacillus* by at least one filtration;
A3. neutralization to pH 6.5-7.5.

4. The process for the preparation and purification of the sodium salt of HA according to claim 3, wherein the inactivation A. of the fermentation broth further comprises a thermal treatment of the fermentation broth by heating for the production of a high- medium- or low-viscosity HA.

5. The process for the preparation and purification of the sodium salt of HA according to claim 4, wherein the thermal treatment is carried out by increasing the temperature of the broth to 60±5° C. for 5-40 minutes for the production of a sodium salt of HA having a final intrinsic viscosity (IV) within the range of 17-24 dl/g.

6. The process for the preparation and purification of the sodium salt of HA according to claim 4, wherein the thermal treatment is carried out by increasing the temperature of the broth to 70±5° C. for 5-40 minutes for the production of a sodium salt of HA having a final intrinsic viscosity (IV) within the range of 10-15 dl/g.

7. The process for the preparation and purification of the sodium salt of HA according to claim 4, wherein the thermal treatment is carried out by increasing the temperature of the broth to 90±5° C. for 150-300 minutes for the production of a sodium salt of HA having a final intrinsic viscosity (IV) within the range of 3-6 dl/g.

8. The process for the preparation and purification of the sodium salt of HA from rooster combs according to claim 1, wherein the extraction step is preceded by a thermal treatment of a homogenate of rooster combs by heating and contemporary enzymatic digestion, for the production of a high-, medium- or low-viscosity HA.

9. The process for the preparation and purification of a sodium salt of HA according to claim 8, wherein the thermal treatment is effected by increasing the temperature to 50-60° C. for 26-30 h to prepare a sodium salt of HA having a final intrinsic viscosity (IV) within the range of 17-24 dl/g.

10. The process for the preparation and purification of a sodium salt of HA according to claim 8, wherein the thermal treatment is effected by increasing the temperature to 60-65° C. for 28-30 h to prepare a sodium salt of HA having a final intrinsic viscosity (IV) within the range of 10-15 dl/g.

11. The process for the preparation and purification of the sodium salt of HA according to claim 8, wherein the thermal treatment is effected by increasing the temperature to 65-70° C. for 46-50 h, for the production of a sodium salt of HA having a final intrinsic viscosity (IV) within the range of 3-6 dl/g.

12. The process for the preparation and purification of the sodium salt of HA from rooster combs according to claim 1, wherein the purification step C. is preceded by a precipitation in ethanol of the sodium salt of HA obtained in the extraction step B., elimination of the solvent and solubilization of the precipitate in purified water.

13. A process for the preparation and purification of the sodium salt of HA from the fermentation broth of *Streptococcus* or *Bacillus* according to claim 1, comprising the following steps:
   A. inactivation of the fermentation broth, comprising the following steps:
      A1. acidification of the broth to pH 4-5;
      A2. possible thermal treatment of the broth, under stirring;
      A3. elimination of the biomass from *Streptococcus* or *Bacillus* by filtration on pads of Celite in an amount of from 20 to 60 g/litre of broth;
      A4. neutralization to pH 6.5-7.5;
   B. extraction, comprising the following steps:
      B1. addition to the filtrate A3 of Celite in an amount of from 20 to 60 g/litre of broth and complexing with CPC 4-20 g/litre, under stirring for at least 30 minutes and subsequent sedimentation for at least a further 30 minutes;
      B2. elimination of the liquid phase;
      B3. solubilization of the HA present in the solid phase in aqueous NaCl 0.3 M under stirring for a period ranging from 4 to 24 h, filtration by means of filters having a filtration degree of 3 μm and collection of the first extract as sodium salt of HA; this procedure B3. being effected from 1 to 4 times;
      B4. joining the extracts;
      B5. addition of an aromatic resin in an amount of from 10 to 60 g/litre of extract, having a pore radius ranging from 200 to 300 Angstrom, to the joined extracts of B4., leaving under stirring for at least 8 h;
      B6. filtrations comprising filtering cloths;
   C. purification, comprising the following steps
      C1. addition of NaOH 0.2-0.4 M in water, under stirring, to the filtered product B6.;
      C2. neutralization to a pH ranging from 8 to 9;
      C3. filtration;
      C4. precipitation and at least one washing of HA sodium salt obtained from step C3., with ethanol, final washing in an organic solvent;
      C5. drying of the sodium salt of HA as known to skilled persons in the field for not less than 15 h, under vacuum.

14. The process for the preparation and purification of the sodium salt of HA from rooster combs according to claim 1, wherein the extraction step B. is preceded by thermal treatment of a homogenate of combs by heating and contemporary enzymatic digestion, for the production of a high- or medium- or low-viscosity HA, comprising the following steps:
   B. extraction, comprising the following steps:
      B1. addition to the enzymatic homogenate of Celite in an amount of from 20 to 60 g/litre of enzymatic homogenate and complexing with CPC in an amount of from 4 to 20 g/litre, under stirring for at least 30 minutes and subsequent sedimentation for at least a further 30 minutes;
      B2. elimination of the liquid phase;
      B3. solubilization of the HA present in the solid phase in aqueous NaCl 0.3 M under stirring for a period ranging from 4 to 24 h, filtration by means of filters having a filtration degree of 3 μm and collection of a first extract as sodium salt of HA; this procedure B3. being effected from 1 to 4 times;
      B4. joining the extracts coming from step/s B3.;
      B5. addition of an aromatic resin in an amount of from 10 to 60 g/litre of extract, having a pore radius ranging from 200 to 300 Angstrom, to the joined extracts of B4, leaving under stirring for at least 8 h;
      B6. filtrations comprising filtering cloths, possibly also filters with a filtration degree of 3 μm;
   C. Purification, comprising the following steps:
      C1. addition of NaOH 0.2-0.4 M in water, under stirring, to the filtered product of B6.;
      C2. neutralization to a pH ranging from 8 to 9;
      C3. filtration;
      C4. precipitation and at least one washing of HA sodium salt obtained from step C3., with ethanol, final washing in an organic solvent;
      C5. drying of the sodium salt of HA, for not less than 15 h, under vacuum.

15. The process for the preparation and purification of the sodium salt of HA from rooster combs according to claim 14, wherein the purification step C. is preceded by a precipitation in ethanol of the sodium salt of HA obtained in the extraction step B., elimination of the solvent and solubilization of the precipitate in purified water.

16. The process for the preparation and purification of the sodium salt of HA according to claim 1, wherein the yield of the process ranges of from 75 to 90% and the maximum values of total proteins and toxins of the sodium salt of the HA obtained are:
   a. 0.05% of proteins;
   b. 0.02 IU/mg of endotoxins.

17. The process for the preparation and purification of the sodium salt of HA according to claim 1 wherein one or more of the following conditions is used:
   i) neutralizing to a pH ranging from 8 to 9 in step C2 is with HCl;
   ii) final washing in an organic solvent in step C4 is with acetone;
   iii) drying of the sodium salt of HA in step C5 is done at between 25 and 40° for not less than 15 h, under vacuum.

18. The process for the preparation and purification of the sodium salt of HA from the fermentation broth of *Streptococcus* or *Bacillus* according to claim 3, wherein in step A1 the acidification is performed with HCl and in step A3 the neutralization is performed with NaOH.

19. The process for the preparation and purification of the sodium salt of HA according to claim 5, wherein the thermal treatment is carried out at 65° C. for 5-30 minutes.

20. The process for the preparation and purification of the sodium salt of HA according to claim 6, wherein the thermal treatment is carried out at 70° C. for 5-30 minutes.

21. The process for the preparation and purification of a sodium salt of HA according to claim 9, wherein the thermal treatment is carried out at 55° C. for 28 h.

22. The process for the preparation and purification of a sodium salt of HA according to claim 10, wherein the thermal treatment is carried out at 60° C. for 30 h.

23. The process for the preparation and purification of a sodium salt of HA according to claim 11, wherein the thermal treatment is carried out at 65° C. for 48 h.

24. The process for the preparation and purification of a sodium salt of HA according to claim 13, wherein one or more of the following conditions is used:
   i) acidification of the broth to pH 4-5 in step A1 is with HCl 1N;
   ii) elimination of the biomass from *Streptococcus* or *Bacillus* in step A3 by filtration on pads of Celite is in an amount of from 30-40 g/l, and filtration with polypropylene filters having a filtration degree of 0.5 μm;
   iii) neutralization to pH 6.5-7.5 in step A4 is with aqueous NaOH at 20%;
   iv) complexing with CPC is with 5-15 g/litre in step B1;
   v) addition of an aromatic resin is with a resin composed of crosslinked polystyrene matrixes in step B5;
   vi) further filtration with polypropylene filters with a filtration degree of 3 μm in step B6;
   vii) neutralizing to a pH ranging from 8 to 9 in step C2 is with HCl;
   viii) filtration in step C3 is with a polypropylene filters having a filtration degree equal to 3 μm;
   ix) final washing in an organic solvent in step C4 is with acetone;
   x) drying of the sodium salt of HA in step C5 is done at between 25 and 40° for not less than 15 h, under vacuum.

25. The process for the preparation and purification of a sodium salt of HA according to claim 14, wherein one or more of the following conditions is used:
   i) complexing with CPC is with 5-15 g/litre in step B1;
   ii) addition of an aromatic resin is with a resin composed of crosslinked polystyrene matrixes in step B5;
   iii) further filtration with polypropylene filters with a filtration degree of 3 μm in step B6;
   iv) neutralizing to a pH ranging from 8 to 9 in step C2 is with HCl;
   v) filtration in step C3 is with a polypropylene filters having a filtration degree equal to 3 μm;
   vi) final washing in an organic solvent in step C4 is with acetone;
   vii) drying of the sodium salt of HA in step C5 is done at between 25 and 40° for not less than 15 h, under vacuum.

* * * * *